United States Patent [19]

Guido et al.

[11] Patent Number: 4,827,964

[45] Date of Patent: May 9, 1989

[54] SYSTEM FOR METERING OF BREATHING GAS FOR ACCOMMODATION OF BREATHING DEMAND

[75] Inventors: Michael R. Guido, Pittsburgh; Ellison L. Davison, Gibsonia, both of Pa.

[73] Assignee: Mine Safety Appliances Company, Pittsburgh, Pa.

[21] Appl. No.: 41,853

[22] Filed: Apr. 23, 1987

[51] Int. Cl.[4] .......... A61M 16/00

[52] U.S. Cl. .......... 137/81.1; 128/204.21

[58] Field of Search .......... 128/204.21; 137/81.1

[56] References Cited

U.S. PATENT DOCUMENTS

| | | | |
|---|---|---|---|
| 3,923,056 | 12/1975 | Bingmann et al. | 128/204.21 |
| 4,579,115 | 4/1986 | Wallroth et al. | 128/204.21 |
| 4,658,397 | 3/1987 | Beale | 137/81.1 |

FOREIGN PATENT DOCUMENTS

| | | | |
|---|---|---|---|
| 0000928 | 2/1987 | World Int. Prop. O. | 128/204.21 |

*Primary Examiner*—A. Michael Chambers

*Attorney, Agent, or Firm*—Reed Smith Shaw & McClay

[57] ABSTRACT

An electronic-breathing mask system uses an electro-pneumatic valve for controlling air flow to a pilot. The system provides a continuous flow of air in an amount proportional to the pressure in the mask. The pressure in the mask is compared against a setpoint pressure to maintain a minimum derived pressure therein.

8 Claims, 5 Drawing Sheets

SYSTEM FOR METERING OF BREATHING GAS FOR ACCOMMODATION OF BREATHING DEMAND

BACKGROUND OF THE INVENTION

The present invention relates to breathing masks. More specifically, the present invention relates to an electro-pneumatic system for controlling the air pressure within a breathing mask.

Demand type breathing apparatus has applications in such areas as medicine, scuba diving and high altitude flight. In the area of high altitude flight, the pilots of modern high-performance aircraft must be equipped with oxygen breathing systems equally capable of high performance. These systems must supply oxygen to the pilot over a broad range of operating conditions, while maintaining rapid response to the pilot's breathing demands. Moreover, a breathing system is required that maintains a positive pressure in the mask, relative to external pressure, so no toxic materials that may be present in the external environment are drawn into the mask. The conventional oxygen regulator which is currently employed to perform these functions is a product of technology which dates back to World War II. This technology will not be able to meet the future needs for ever-greater regulator performance and integrating with overall pilot life-support systems. These oxygen regulators rely on mechanical elements, such as lever arms and springs. In such regulators, some force must be applied to a closed valve in order for it to be opened and for air to be supplied. In a conventional regulator of this type, the only available source of this force is the breathing demand of the regulator user. By inhaling, the user creates a pressure differential across a diaphragm or other sensing member, resulting in the operating force. Generally, this force is lesser in magnitude than that normally required to open the valve; therefore, some device which multiplies the available force, such as a lever arrangement, is commonly used. However, because of the law of mechanical advantage, such devices will reduce the magnitude of the possible valve opening, to the same degree which they increase the available force. Since the maximum flow capability of the regulator is directly dependent upon the valve opening, this inherently limits the performance for a given diaphragm size. One can, of course, increase the diaphragm size, but in applications where space is of the essence, this is not practical. Alternate mechanical approaches have been developed, for example the balanced valve or the pilot valve, but each of these has other problems such as oscillations in the system, or the need for two steps to open the valve, respectively. Additionally, inherent in these types of mechanical systems is a lag in the response of the valve to open upon demand.

Electro-pneumatic systems do not suffer from any of the problems present in mechanical systems. Any forces necessary to open a valve are achieved through electromagnetic means, with basically a large force being achieved with, for instance a large current, in a given space. There have been attempts to produce an adequate electro-pneumatic breathing system. But, a severe problem present in them is the air supplied to the face mask is not continuous due to the servo valve not providing a linear response to a central signal which corresponds to the air pressure in the mask being greater than or less than a minimum desired pressure as a function of time. For example, United Kingdom Patent Application No. GB 2154887 (September 1985) discloses a breathing apparatus that is servo-controlled. Therein, a three-way valve comprises a circular valve member surrounded by an O-ring. The O-ring has three ports, the first port being 90° apart from the second, the second being 90° apart from the third, and the third being 180° apart from the first. The valve member is solid except for a channel with a 90° bend at the center running therethrough. In operation, the valve member is turned to a desired position by an actuator. If the pressure in the mask is too little (user inhaling), the valve rotates so the channel therein connects port 1 (connected to an air supply) and port 2 (connected to the mask) to allow air to enter the mask and raise the pressure. If the pressure in the mask is too great (user exhaling) then the valve member rotates to connect port 2 and port 3 (connected to an exhaust channel) to allow excess air to escape from the mask and reduce the pressure. The actuator operates according to a control unit that receives a signal from a pressure transducer in the mask. When the pressure is below a predetermined level, ports 1 and 2 are connected. When the pressure is above a predetermined level, ports 2 and 3 are connected. The problem with this device though, is either air is supplied or is not supplied, but there is no ability to provide air in proportion to the demand of a user.

Additional approaches have attempted to take into account all the components, i.e., g-forces, altitude, in calculating the pressure supplied, but do not deal with an electro-pneumatic system controlling the actual breathing supply. See, "Altitude and Acceleration Protection System for High Performance Aircraft" by A. Gupta and M. McGrady, Boeing Military Airplane Company, under USAF Contract F33615083-C-0651.

SUMMARY OF THE INVENTION

Accordingly one object of the present invention is to provide a near constant air pressure inside a face mask.

Another object of the present invention is to provide air or other breathing gas, such as oxygen, to the face mask of a pilot or other user as needed without the pilot or other user experiencing any lag between the time he begins to inhale and the time that he receives air.

These and other objects of the present invention are attained with a demand breathing apparatus comprising an air tight mask having an air supply port; a pressure transducer disposed to detect the air pressure inside the mask; means for producing an electrical signal proportional to the magnitude of the difference between the detected pressure in the mask and the desired pressure if the detected pressure in the mask is less than a desired pressure; and means for continually supplying air to the mask through the supply port in proportion to the signal.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, where.

DESCRIPTION OF THE PREFERRED EMBODIMENTS

Figure 1:
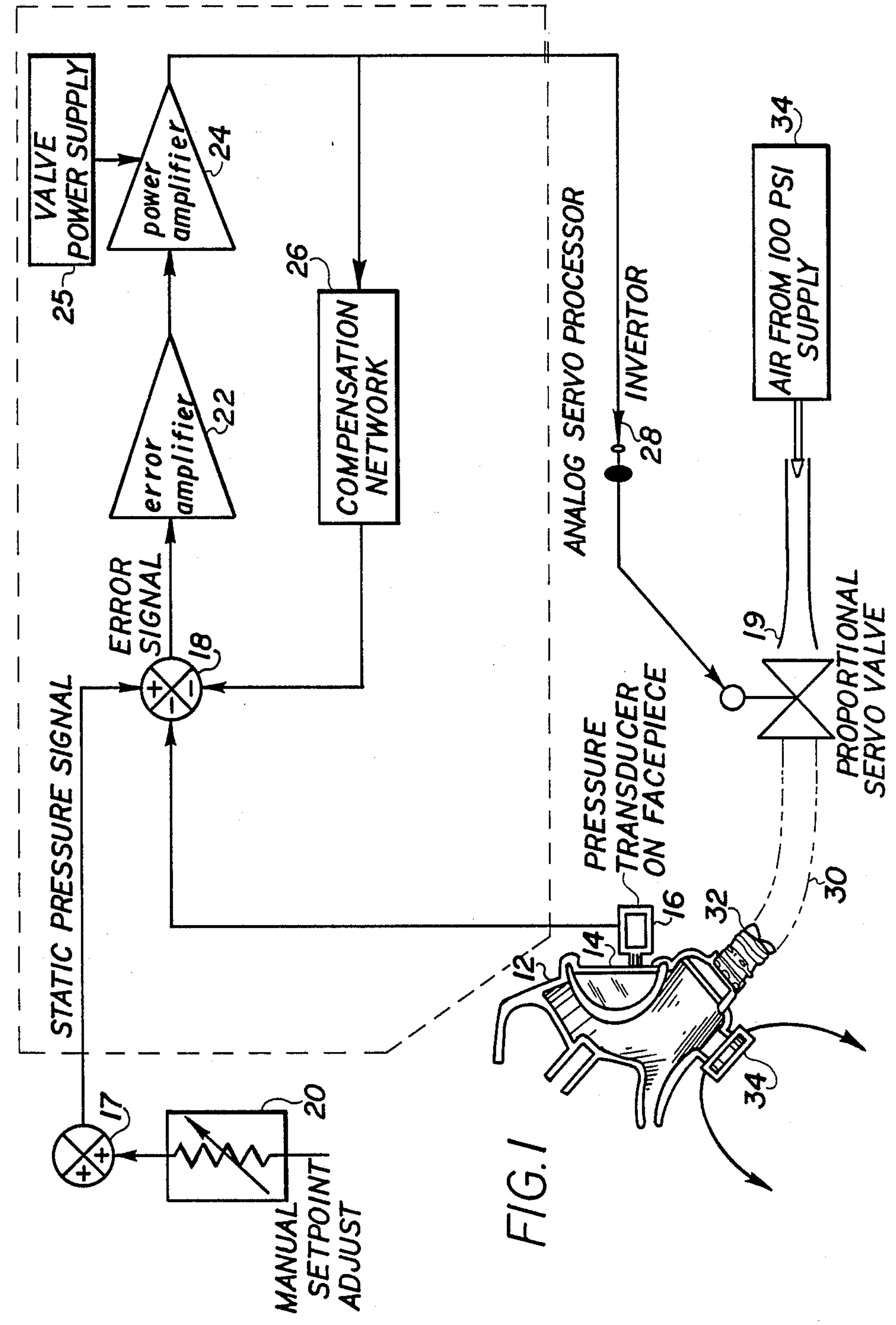
FIG. 1 is a schematic diagram of the electronic mask breathing apparatus.
Figure 2:
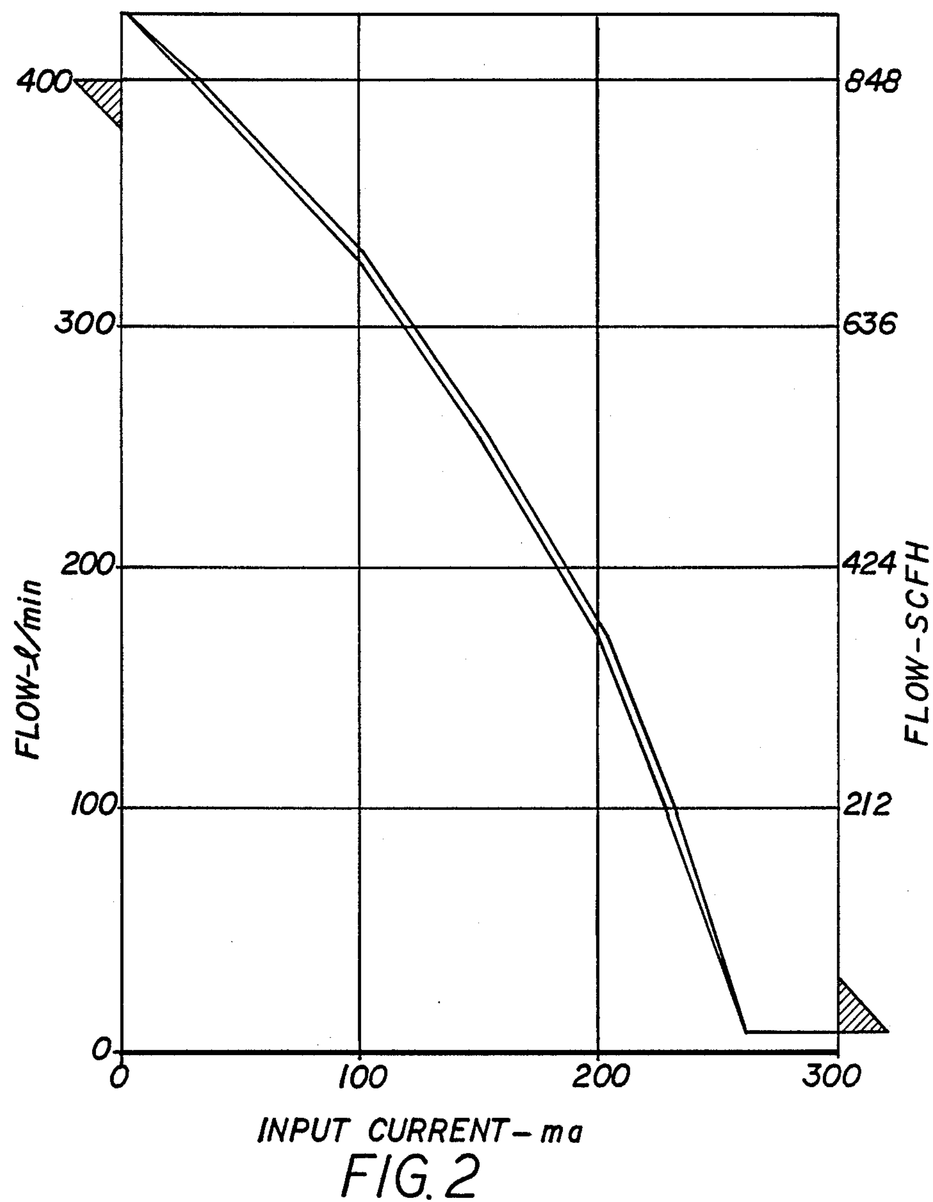
FIG. 2 is a graph of the servo-valve opening as a function of current.

Referring to the drawings, wherein like reference numerals designate identical or corresponding parts throughout, and more particularly to FIG. 1 thereof, numeral 10 designates a system for the metering of breathing function for accommodation of breathing demand. The system 10 is comprised of a mask 12 that is fitted over and is placed on at least the nose and mouth of a pilot (not shown). On the face plate 14 of the mask 12 is a pressure transducer 16 that detects the pressure inside the face mask 12. The pressure detected by the transducer 16 is compared to a setpoint pressure value produced by a setpoint voltage source 17 in a voltage comparator 18. If the pressure detected by the transducer 16 is greater than the setpoint pressure (the situation corresponding to a pilot exhaling), the servo valve that controls the flow of air to the mask 12 from a pressurized air supply (not shown) is closed if it is open, or maintained shut if it is already closed. If the pressure in the face mask 12 is less than the set point pressure (the situation corresponding to a pilot inhaling), then the servo valve 19 is opened by an amount proportional to the magnitude of the difference between the pressure in the mask 12 and the setpoint pressure. In this way a pilot is supplied air in a linear fashion and in an amount proportional to the pilot's demand.

More specifically, the face mask 12 fits securely and forms an air tight seal over the face of a pilot. A pilot's mask is generally a half-mask covering only the nose and mouth—note that the system can work with either type of mask described depending upon the application. On the top of the face plate or at some other point out of the line of sight of the pilot is one port (not shown) of a transducer which penetrates through the face plate and communicates with the interior of the face mask. A second or referece port, not shown, is located on the outside of the transducer 16 to detect the pressure of the atmosphere external to the face plate 12. The difference between the internal and external pressures is determined by the transducer and a signal having a voltage corresponding to this difference is produced. Such pressure transducers and their operation are well known in the art. See, "Machine Design" Magazine, 5/15/86, "Pressure Sensors", for a more detailed discussion of this subject.

While the transducer 16 is continuously determining the pressure in the face mask 12 a voltage source 17 is producing a constant signal having a set voltage corresponding to a desired pressure level. This pressure level will depend upon the projected use requirements of the apparatus. For a pilot in an aircraft at rest, this level would be set equal to ambient conditions. In a commercial application of such a breathing apparatus, this pressure level would be set at a level no less than ambient pressure, and no greater than a positive pressure of 1.5 inches of water. This is a statutory limitation enforced by NIOSH (see the Code of Federal Regulations 10 C.F.R. 30, Part 11, Subpart H). It applies to open-circuit pressure demand breathing apparatus for use in hazardous atmospheres.

The transducer signal and the set point signal are then compared in a voltage comparator 18. Of course, for proper comparison, the two signals must be identical for a given pressure. This can be accomplished by choosing the proper voltage source 17, which produces essentially the same voltage signal as the transducer 16, and also electrically connecting a potentiometer 20 to the voltage source. The potentiometer 20 enables the voltage of the set point signal to be tuned to calibrate with the transducer signal at a given pressure. For instance, 1.5 inches of water could correspond to a voltage of 3 mv produced by the transducer 16. For the set point voltage to correspond to 1.5 inches of water it must also have a voltage of 3 mv, which can be obtained by adjusting the potentiometer 17 accordingly. Referring again to the voltage comparator 18, it measures the difference in the voltages of the two signals and produces a signal corresponding to the magnitude of the difference as well as the sign of the difference (+or −) between the voltage corresponding to the mask pressure and the setpoint voltage. Such a comparator 18 is well known in the art. See, National Semiconductor Corporation's "Linear Data Book", Section 5, "Voltage Comparison", for a discussion of the operation of a comparator 18. Note, that comparator 18 is essentially identifying the error in the face mask 12 from the desired pressure. Thus, if the pressure is greater in the mask 12 than the setpoint pressure, a positive signal with a magnitude results. If the pressure in the mask is less than the setpoint pressure, a negative signal with a magnitude results.

An error amplifier 22 then receives the signal produced by the voltage comparator and adjusts the error signal to be able to be amplified by a power amplifier 24. The power amplifier 24 provides sufficient current to operate a servo valve 19. A valve power supply 25, such as a portable battery provides the energy to the power amplifier 24 to produce adequate current to operate the servo valve 19. A compensation network 26 provides additional feedback to the voltage comparator 18 to dampen various oscillations in the output signal of the power amplifier 24 that are inherent in the system. The compensation network 26 can, for instance, be a capacitor.

Figure 3:
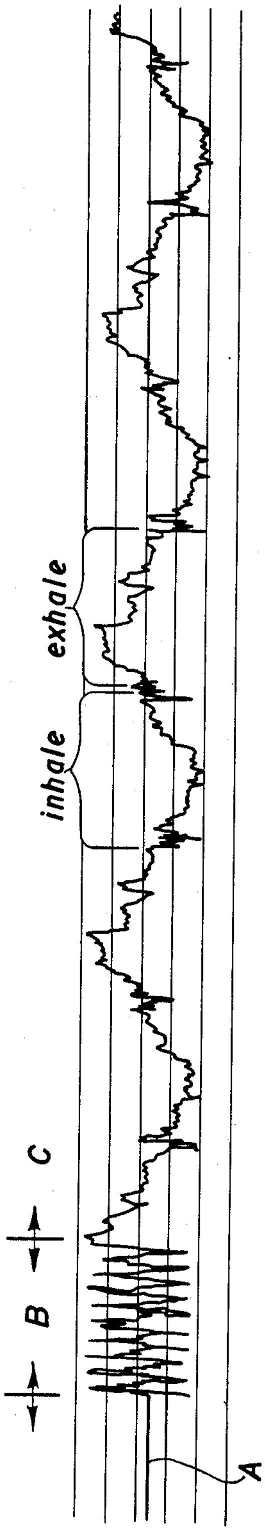
FIG. 3 is a printout of the pressure in the face mask of the breathing system under simulated breathing conditions.

The proportional servo valve 19 provides a linear response to the control signal produced by the power amplifier. The signal produced by the power amplifier 24 in turn is proportional to the signal produced by the voltage compensator 18 that identifies the error magnitude and sign between the pressure in the mask and the desired setpoint pressure. Thus, the valve 19 opens only an amount proportional to the error magnitude. In other words, the lower the pressure in the mask 12, the greater the error magnitude and the larger the valve 19 opens. If the error magnitude is positive, the value does not open at all. FIG. 3 shows a graph representing the specific response of, for example an HSC servo valve 19, Part No. 70A-121, as a function of current. Note that the response indicates the valve opens less the greater the current, so for this type of valve 19, an inverter 28 must be placed before valve 19, through which the signal from the power amplifier must pass before operating the valve 19.

The valve 19 is situated at the outlet of an air supply channel or hose 30 that receives air from, for instance, a 100 PSI air source. Any air supply having a pressure at least greater than the set point pressure is sufficient, but an air supply should be at a high enough pressure to overcome the maximum depressurization in the mask 12 resulting from inhalation and still maintain a positive pressure therein during such time. FIG. 3 is a printout of the pressure in the mask 12 of the system 10 during the breathing cycle of a simulated human being, Part A of the printout shows constant pressure corresponding to the setpoint pressure. Part B of the printout shows the pressure in the mask 12 of the system 10 during the simulated breathing corresponding to a human being. Part C also shows the pressure in the mask 12 during a simulated breathing situation, with a greatly expanded time base. Note that the pressure decreases during the inhalation phase and increases during the exhalation phase, but never falls to zero or negative pressure. The printout of part C is essentially sinusoidal in form, as is the breathing pattern of a human being.

Lastly, the regulator outlet channel is attached to the mask 12 at location 32 to allow air from the air supply 34 to enter the mask 12. Air exhalation valve 34 allows air to pass out of the mask 12 when the pressure in the mask is greater than a pre-determined level.

Figure 5:
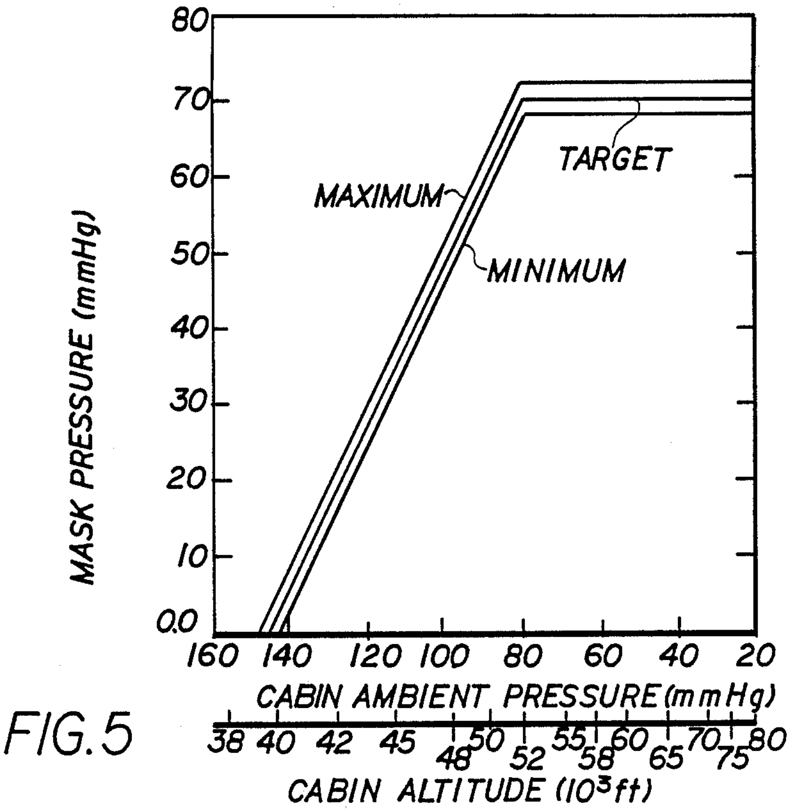
FIG. 5 is a graph of the pressure schedule for altitude protection.
Figure 6:
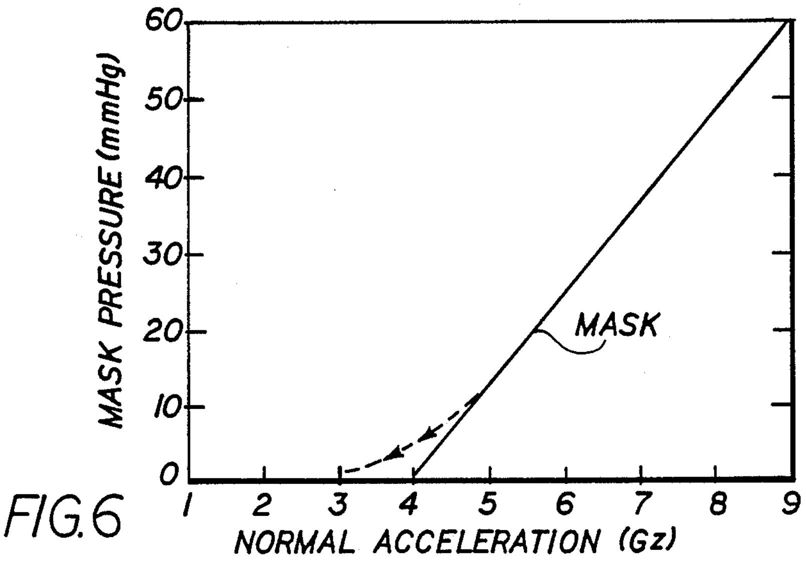
FIG. 6 is a graph of the pressure schedule for acceleration protection.

An additional feature of the breathing system is a logic circuit 100 that varies the desired pressure in the mask 12 according to various external circumstances. For instance, the air force requires different pressures of air to be supplied to a pilot or other user as a function of altitude. The greater the altitude, the greater the pressure in the mask should be. FIG. 5 sets out the U.S. Air Force required mask pressure versus operational altitudes (in mm. of $H_g$), while FIG. 6 gives the Air Force mask pressure requirements for varying G-force levels. These figures are derived from the Statement of Work included in USAF Contract F33615-83-C0651, "Tactical Life Support System".

Figure 4:
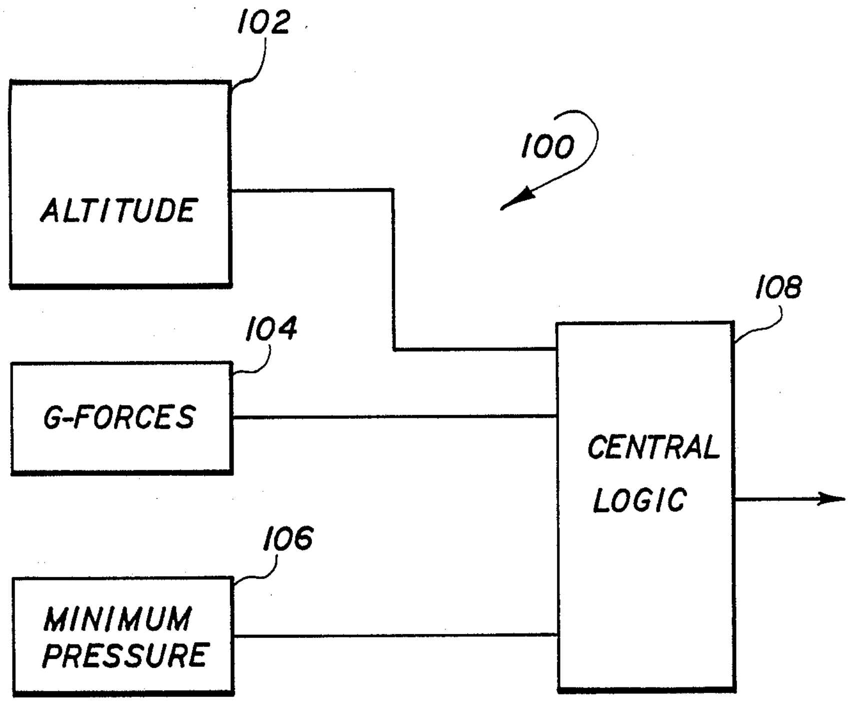
FIG. 4 is a schematic diagram of the logic circuit controlling the setpoint voltage.

Referring to FIG. 4 there is shown a block diagram of the logic circuit 100 that changes the desired setpoint pressure. The circuit 100 is comprised of inputs, such as altitude 102 of the plane and G-forces 104 experienced by the plane at any point in time. These two inputs can be, for instance, table look-up devices that produce a voltage. corresponding to a predefined value that is detected. The altitude input 102 can have an altitude sensor associated with it that causes a corresponding voltage signal to be produced depending on the altitude sensed. Typically, and in accordance with Table 1, the greater the altitude, the greater the magnitude of the voltage signal. Similarly, the G-force input 104 consists of a G-force detector that causes the G-force input 104 to be of a greater voltage the greater the G-force sensed. There also is a fixed voltage source 106 that corresponds to a minimum desired pressure in the mask 12.

Each of the inputs feed into a central logic 108 which essentially chooses the highest inputted voltage signal as the desired setpoint voltage signal. The higher the setpoint voltage signal, the greater the corresponding pressure in the mask 12. Thus, the condition that evokes the highest signal is adequately met in regard to user demand. In the embodiment where the logic circuit 100 is used, the voltage source 17 is the voltage signal passed by the circuit 100. The manual setpoint adjustment 20 modifies the voltage signal from the circuit 100 to correspond with a desired pressure in the mask 12 at, for example, sea level with one G-force present.

Obviously, numerous (additional) modifications and variations of the present invention are possible in light of the above teachings. It is therefore to be understood that within the scope of the appended claims, the invention may be practiced otherwise than as specifically described herein.

We claim:

1. A demand breathing apparatus comprising:

an air tight breathing mask having an air supply port;

an air supply channel connected to the supply port;

a pressure-sensitive transducer disposed to detect the air pressure inside the mask and produce a voltage corresponding to the detected inside pressure;

a voltage source to provide a voltage corresponding to a set point pressure;

means for calibrating the voltage produced by the voltage source to correspond with a given pressure detected by the transducer;

a voltage comparator electrically connected to the calibrating means and the transducer to determine if the difference of the voltage of the transducer is less than the voltage of the calibrated voltage source, and to determine the magnitude of the difference, and if the transducer voltage is less than the calibrated voltage source voltage produce a current corresponding to the determined magnitude of the difference; and an electro-pneumatic servo-valve electrically connected to the voltage comparator to receive the current from the voltage regulator, and also connected to the supply channel to allow air to pass therethrough and into the mask in proportion to the received current.

2. An apparatus as described in claim 1 including a power amplifier means electrically connected between the voltage comparator and the servo valve for the purpose of amplifying the current produced by the voltage comparator sufficiently to cause the servo valve to allow a desired amount of air to pass.

3. An apparatus as described in claim 2 including a compensation network electrically connected between the servo valve and the power amplifier means for the purpose of providing feedback to the voltage comparator in order to dampen oscillations in the current controlling the servo valve and cause a more accurate current corresponding to a desired air pressure to pass to the servo valve.

4. An apparatus as described in claim 3 wherein the power amplifier means includes a power amplifier electrically connected to the voltage comparator, an error amplifier electrically connected to and between the voltage comparator and the power amplifier for the purpose of preparing the current signal from the voltage comparator to be amplified by the power amplifier, and an electrical source electrically connected to the power amplifier to provide energy to the power amplifier.

5. An apparatus as described in claim 4 wherein the electrical source is a battery.

6. An apparatus as described in claim 1 wherein the calibration means is a potentiometer electrically connected between the voltage source and the voltage comparator.

7. A demand breathing apparatus comprising:

an air tight breathing mask having an air supply port;

an air supply channel connected to the supply port;

a pressure-sensitive transducer disposed to detect the air pressure inside the mask and produce a voltage corresponding to the detected inside pressure;

an altitude sensor;

means for producing a voltage signal corresponding to the altitude sensed;

G-force sensor;

means for producing a voltage signal corresponding to the G-forces sensed;

a fixed voltage source producing a voltage signal corresponding to a minimum desired pressure;

control logic means electrically connected to receive the voltage signals of the altitude voltage signal means, G-force voltage signal means and fixed voltage signal means, said control logic means allowing the largest voltage signal received to correspond to the desired pressure in the mask;

means for calibrating the voltage signal received from the control logic means to correspond with a given pressure detected by the transducer, said calibrating means electrically connected to the control logic means;

a voltage comparator electrically connected to the calibrating means and the transducer to determine if the difference of the voltage of the transducer is less than the voltage from the control logic means, and to determine the magnitude of the difference, and if the transducer voltage is less than the control logic means voltage produce a current corresponding to the determined magnitude of the difference; and an electro-pneumatic servo-valve electrically connected to the voltage comparator to receive the current from the voltage regulator, and also connected to the supply channel to allow air to ass therethrough and into the mask in proportion to the received current.

8. An apparatus as described in claim 7 wherein the calibration means is a potentiometer electrically connected between the control logic means and the voltage comparator.

* * * * *